(12) United States Patent
Mannan et al.

(10) Patent No.: US 8,460,679 B2
(45) Date of Patent: Jun. 11, 2013

(54) GLYCOLIPID ADJUVANT COMPOSITIONS

(75) Inventors: Ramasamy M. Mannan, Kalamazoo, MI (US); Paul J. Dominowski, Hickory Corners, MI (US); Sangita Mediratta, Portage, MI (US)

(73) Assignee: Zoetis LLC, Florham Park, NJ (US)

( * ) Notice: Subject to any disclaimer, the term of this patent is extended or adjusted under 35 U.S.C. 154(b) by 572 days.

(21) Appl. No.: 11/698,335

(22) Filed: Jan. 26, 2007

(65) Prior Publication Data

US 2007/0196384 A1 Aug. 23, 2007

Related U.S. Application Data

(60) Provisional application No. 60/762,279, filed on Jan. 26, 2006, provisional application No. 60/814,984, filed on Jun. 20, 2006.

(51) Int. Cl.
*A61K 39/295* (2006.01)
*A61K 39/02* (2006.01)

(52) U.S. Cl.
USPC .................................. 424/201.1; 424/234.1

(58) Field of Classification Search
None
See application file for complete search history.

(56) References Cited

U.S. PATENT DOCUMENTS

| 4,291,019 A * | 9/1981 | Lupton et al. ............. 424/229.1 |
| 4,686,208 A | 8/1987 | Lockhoff |
| 4,737,488 A | 4/1988 | Lockhoff |
| 4,855,283 A | 8/1989 | Lockhoff |
| 5,718,904 A | 2/1998 | Hjorth |
| 5,837,250 A | 11/1998 | Kandil |
| 6,290,971 B1 | 9/2001 | Kandil |
| 6,491,951 B1 | 12/2002 | Af Ursin et al. |
| 6,764,682 B1 | 7/2004 | Kandil |
| 2004/0028698 A1 | 2/2004 | Colau et al. |

FOREIGN PATENT DOCUMENTS

| AU | 637355 | 10/1990 |
| JP | 2-292221 | 12/1990 |
| JP | 8-325163 | 12/1996 |
| JP | 2002-532438 | 10/2002 |
| JP | 2004-510747 | 4/2004 |

OTHER PUBLICATIONS

Lockhoff, O., "Glycolipids as Immunomodulators: Syntheses and Properties," Angew. Chem. Int. Ed. Engl., 30, pp. 1611-1620, 1991.
Lockhoff, O and Hayauchi, Y., "Synthesis of Peptidoglycolipid Analogs with Distinct Immunomodulating Activities," J. Carbohydrate Chemistry, 19(4&5), pp. 603-619, 2000.
Stunkel, K. G., et al., "In Vitro Studies of Synthetic Glycolipids: A New Class of Compounds with Immunomodulating Activity," Lymphocyte Activation and Differentiation, (J.C. Mani and J. Dorn eds.) de Gruyter, Berlin, pp. 421-425, 1988.
Stunkel, K. G., et al., "Synthetic Glycolipids; In vitro Characterization of a New Class of Compounds With Immunomodulating Properties," Adv. in the Biosci. (Oxford) 68, pp. 429-437, 1988.
Stunkel, K. G., et al., "Synthetic Glycolipids With Immunopotentiating Activity on Humoral Immunity: Evaluation In Vivo," Cellular Basis of Immune Modulation, pp. 575-579, 1989.

* cited by examiner

*Primary Examiner* — Marcela M Cordero Garcia
(74) *Attorney, Agent, or Firm* — Vyacheslav V. Vasilyev

(57) ABSTRACT

This invention relates to compositions and methods of preparing stable adjuvant diluent stock solutions and final adjuvant solutions comprising glycolipids, weak acids, alcohols, nonionic surfactants and buffers.

19 Claims, 1 Drawing Sheet

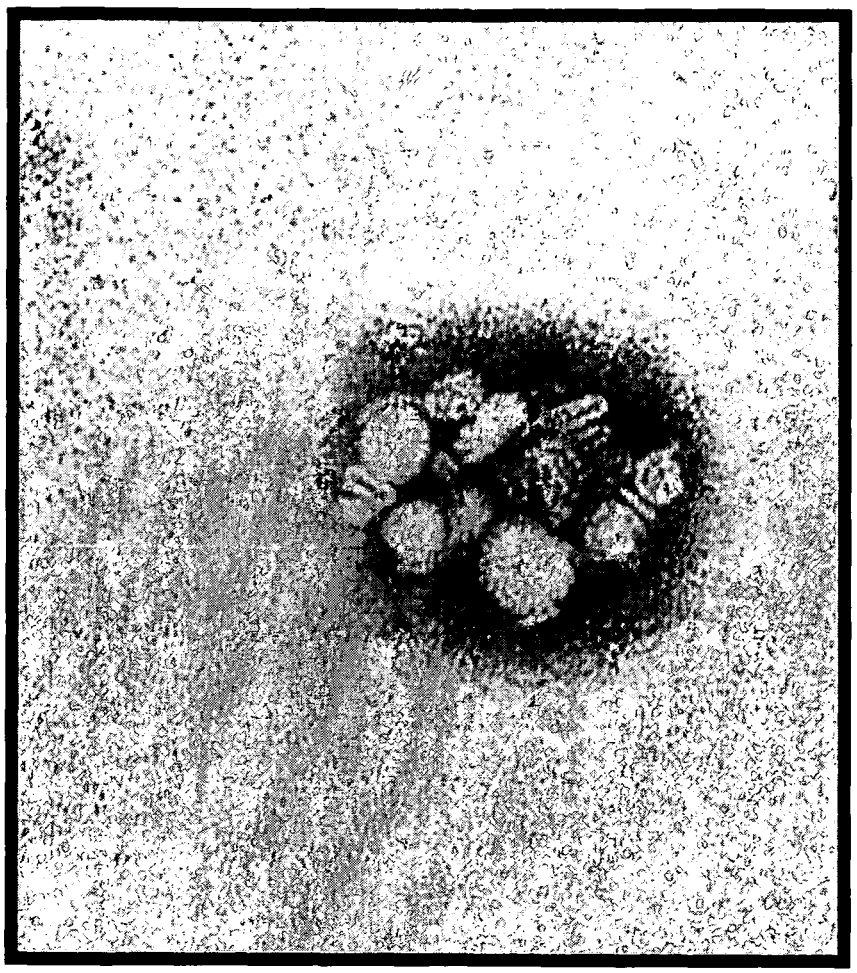

GLYCOLIPID ADJUVANT COMPOSITIONS

CROSS REFERENCE TO RELATED APPLICATION

This application claims the benefit of U.S. provisional patent applications U.S. Ser. No. 60/762,279, filed 26 Jan. 2006, and U.S. Ser. No. 60/814,984, filed 20 Jun. 2006, under 35 USC 119(e)(i), incorporated herewith in their entirety.

FIELD OF THE INVENTION

The present invention relates to novel compositions of glycolipid adjuvants, methods for their use, and their preparation. The novel compositions of the present invention are stable for a long duration without flocculation. They are particularly useful in the delivery of various medicines, including vaccines.

BACKGROUND OF THE INVENTION

Vaccines are typically used to protect humans and veterinary animals from infectious diseases caused by bacteria, viruses and parasitic organisms. The antigens used in vaccines may be any variety of agents but are typically composed of killed pathogenic organisms, pathogenic organisms which are alive but modified or attenuated, proteins, recombinant proteins or fragments thereof. Whatever the source of the antigen, it is often necessary to add an adjuvant to enhance the host immune response to the antigen.

Adjuvants are used to accomplish two objectives: they slow the release of the antigens from the injection site and they stimulate the immune system.

The first adjuvant reported in the literature was Freund's Complete Adjuvant (FCA). FCA contains a water-in-oil emulsion and extracts of mycobacterium. The mycobacterium extracts provide immunostimulatory molecules in a crude form. The water-in-oil emulsion acts to create a depot effect where the antigens are slowly released. Unfortunately FCA is poorly tolerated and it can cause uncontrolled inflammation. Since the discovery of FCA over 80 years ago efforts have been made to reduce the unwanted side effects of adjuvants.

Glycolipid analogues comprising a new class of compounds having adjuvant properties are now known. U.S. Pat. No. 4,855,283, (hereinafter '283) discloses the synthesis of glycolipid analogues, including N-glycosylamides, N-glycosylureas, N-glycosylcarbamates, and specifically: N-(2-deoxy-2-L-leucylamino-β-D-glucopyranosyl)-N-octadecyldodecanamide acetate (known as Bay R1005®, O Lockhoff, Angew. Chem. Int. Ed. Engl. (1991) 30:1611-1620. The compounds described in the '283 patent are particularly suitable for use as adjuvants.

Glycolipid adjuvant formulations need to be easy to manufacture and stable when stored for long periods of time without showing flocculation of the lipid component. The non-acetate forms of the glycolipid amides or glycosylamides are highly insoluble and typically flocculate out of solution upon storage either at room or lower temperatures.

The solutions and adjuvants comprising glycosylamides provided here show little flocculation and are quite stable. They are easy to manufacture and can be prepared on a commercial scale. The liquid glycolipid adjuvant formulations can be used as a diluent to rehydrate a lyophilized antigen preparation. Methods to test the stability of these formulations in real time and through accelerated stability testing protocols are also provided.

SUMMARY OF THE INVENTION

This invention comprises the composition and method of making or manufacturing both Glycosylamide Stock Solution and Glycolipid Adjuvant Solution. The Glycosylamide Stock Solution is prepared by dissolving a glycolipid of Formula I in an alcohol and combining this with an appropriate amount of a weak acid plus a "non-ionic" surfactant. The weak acid is added to the glycolipid alcohol solution, in molar excess of weak acid with reference to the glycolipid. In one embodiment the glycolipid is N-(2-deoxy-2-L-leucylamino-β-D-gulucopyranosyl)-N-octadecyldodecanoylamide hydroacetate. In one embodiment, the alcohol is ethanol. In one embodiment, the weak acid is acetic acid. In one embodiment, the non-ionic surfactants are various sorbitans (SPAN®) or polyoxyethylenesorbitans (TWEEN®) in particular the monolaurate sorbitans (SPAN® 20) and monolaurate polyoxyethylene sorbitans (TWEEN® 20).The Glycolipid Adjuvant Solution is prepared by introducing an appropriate amount of the Glycosylamide Stock Solution into a "suitable buffer." The pH of the final stable Glycolipid Adjuvant Solutions described here should be between about 6 and about 8. A final pH of between about 6 to about 7 is preferred. A final pH between about 6.3 to about 6.4 is described. High salt concentrations of Glycolipid Adjuvant, those in excess of 30 mM NaCl, should be avoided.

These two solutions are exemplified in more detail as follows:

The Glycosylamide Stock Solution is a composition comprising:
  a) a glycolipid of Formula I;
  wherein Formula I is

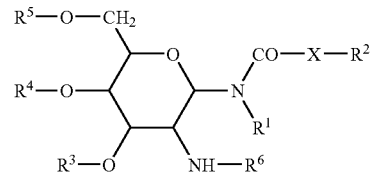

wherein
  $R^1$ is hydrogen, or saturated alkyl radical having up to 20 carbon atoms;
  X is —$CH_2$—, —O— or —NH—;
  $R^2$ is hydrogen, or a saturated or unsaturated alkyl radical having up to 20 carbon atoms;
  $R^3$, $R^4$, and $R^5$ are independently hydrogen, —$SO_4^{2-}$, —$PO_4^{2-}$, —$COC_{1-10}$alkyl;
  $R^6$ is L-alanyl, L-alpha-aminobutyl, L-arginyl, L-aspariginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers;
  in a salt form, where the salt form is derived from a weak acid;
  b) an alcohol wherein the alcohol is HO—$C_{1-3}$ alkyl;
  c) a weak acid, wherein 1) the weak acid is in molar excess with reference to the glycolipid content, and 2) is any acid having a pKa value between about 1.0 and about 9.5 using standard tables or values; and
  d) a non-ionic surfactant, where the non-ionic surfactant is an agent that reduces the surface tension of the material it is dissolved in and has one component that is hydrophobic and another component that is hydrophilic.

The Glycolipid Adjuvant Solution is a composition comprising:
  a) a Glycosylamide Stock Solution; and
  b) a suitable buffer, where the buffer is one appropriate for veterinary or medical use and can maintain a relatively constant pH in an aqueous solution of between about 6.0 and about 8.0.

DETAILED DESCRIPTION OF THE INVENTION

Unless otherwise stated, the following terms used in the specification and claims have the meanings given below.

The term "alcohol" refers to a compound of formula: HO—$C_{1-3}$ alkyl, It may be methanol, ethanol, or propanol in any form, such as n-propanol or iso-propanol. Ethanol is preferred.

The term "alkyl" refers to both straight and branched saturated hydrocarbon moieties.

The term "glycolipids" refers to the compounds of Formula I below. These compounds are described in U.S. Pat. Nos. 6,290,971, and 4,855,283, issued Aug. 8, 1989. Both U.S. Pat. Nos. 6,290,971, and 4,855,283 are hereby incorporated by reference in their entirety. A glycolipid described in particular here, when in its acetate form has the trade name BAY R1005®, and the chemical name "N- (2-deoxy-2-L-leucylamino- β -D-glucopyranosyl)-N-octadecyldodecanamide acetate." The amide form of this compound has the trade name BAY 15-1583® and the chemical name "N-(2-deoxy-2-L-leucylamino- β -D-glucopyranosyl)-N-octadecyldodecanamide."

The glycolipids of Formula I are:

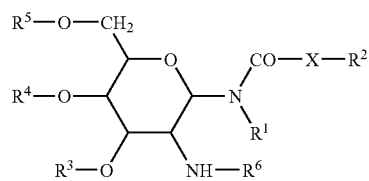

Formula I wherein $R^1$ is hydrogen, or saturated alkyl radical having up to 20 carbon atoms;

X is —$CH_2$—, —O— or —NH—;

$R^2$ is hydrogen, or saturated or unsaturated alkyl radical having up to 20 carbon atoms;

$R^3$, $R^4$, and $R^5$ are independently hydrogen, —$SO_4^{2-}$, $PO_4^{2-}$, or —$COC_{1-10}$alkyl;

$R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers;

or a pharmaceutically acceptable salt thereof.

Another specified embodiment describes the glycolipids of Formula I wherein:

$R^1$ is hydrogen, or saturated $C_{12-18}$ alkyl;
$R^2$ is hydrogen, or saturated $C_{7-11}$ alkyl;
X is —$CH_2$—;
$R^4$, and $R^5$ are independently hydrogen;
$R^6$ is selected from L-leucyl, The variables for Formula I are separate and independent and all combinations of variables are herein described and claimed.

In another embodiment, the glycolipids are those described by Formula II(a):

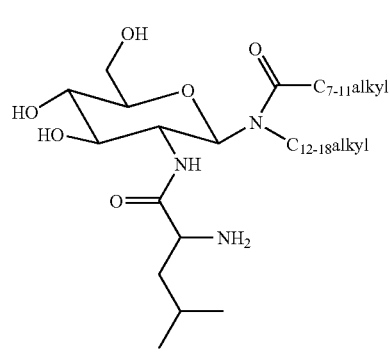

Formula II(a)

In another embodiment, the glycolipids are those described by Formula II(b):

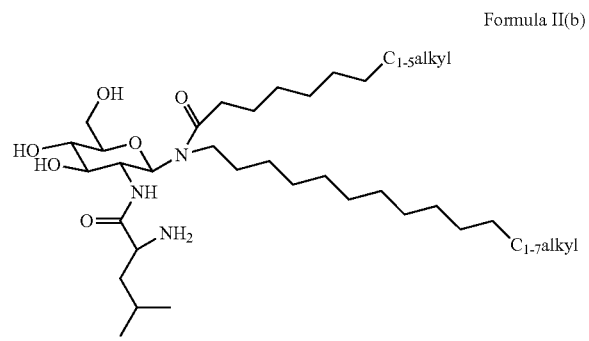

Formula II(b)

In another embodiment, the glycolipids have the structure of Formula III:

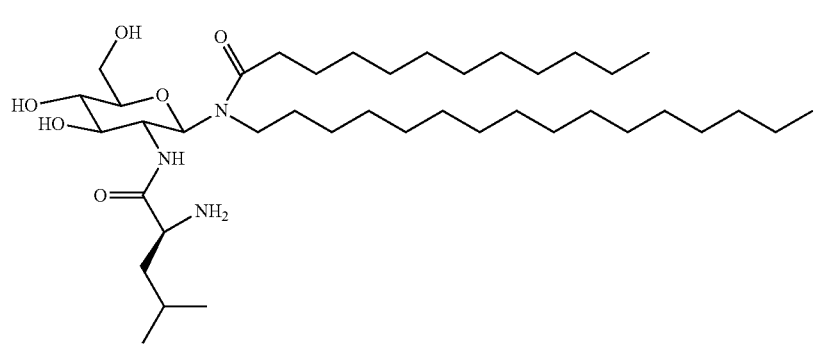

Formula III

A compound of Formula III can exist in either amide form or acetate form. The amide form of this compound has the trade name BAY 15-1583®. The acetate form has the trade name BAY R1005®.

The glycolipids of Formula I can be made using the following procedures, taken from U.S. Pat. No. 4,855,283.

As can be seen from Formula I, the compounds according to the invention are based on a substituted 2-amino-2-deoxyhexose. These sugars are always N-glycosidically bonded via C-1, the anomeric carbon atom, to the acylamido, carbamido or alkoxycarbonylamido group

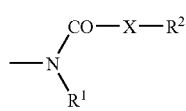
(I)

with the above mentioned meanings for $R^1$, $R^2$ and X.

The 2-amino group of the amino sugars in the compounds according to the invention, of the formula I, is amidically bonded to an α-amino acid or an α-amino acid derivative.

Amino acids are the natural L-amino acids such as glycine, sarcosine, hippuric acid, alanine, valine, leucine, isoleucine, serine, threonine, cysteine, methionine, ornithine, citrtilline, arginine, aspartic acid, asparagine, glutamic acid, glutamine, phenylalanine, tyrosine, proline, tryptophan and histidine. Also described are D-amino acids, such as D-alanine, or amino carboxylic acids, such as alpha-aminobutyric acid, α-aminovaleric acid, α-aminocaproic acid or α-aminoheptanoic acid, both in the D-and the L-form, to act as substituents on the amino sugar.

The processes for the preparation of the compounds according to Formula I are also provided. This entails starting from a 2-amino-2-deoxyglycopyranose derivative (Formula IV), which is protected on the amino group,

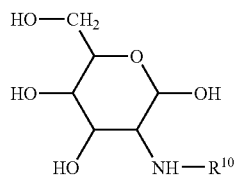
(IV)

in which $R^{10}$ represents a protective group for the protection of amino groups, which is known from the synthesis of peptides and can, where appropriate, be selectively eliminated. Examples of suitable protective groups are acyl groups, such as trifluoroacetyl or trichloroacetyl, o-nitrophenylsulphenyl, 2,4-dinitrophenylsulphenyl or optionally substituted tower alkoxycarbonyl groups such as methoxycarbonyl, t-butyloxycarbonyl, benzyloxycarbonyl, p-methoxybenzyloxycarbonyl or 2,2,2-trichloroethyloxycarbonyl groups. Suitable N-protected amino-hexose derivatives are known. For example, M. Bergmann and L. Zervas, Ber. 64, 975 (1931); D. Horton, J. Org. Chem. 29, 1776 (1964); P. H. Gross and R. W. Jeanloz, J. Org. Chem. 32, 2759 (1 967); M. L. Wolfrom and H. B. Bhat, J. Org. Chem. 32, 1821 (1967); general: J. F. W. McOmie (Editor). Prot. Groups. Org. Chem., Plenum Press (1973); Geiger in "The Peptides" Vol. 3, p 1-99, (198 1) Academic Press; and Literature cited there). Preferred amino protective groups for the preparation of the compounds according to Formula I are the BOC group (tert. butyloxycarhonyl) or the Z group (benzyloxycarbonyl).

The blocked amino sugar derivatives (IV) are reacted, in a first reaction step, with amines (Formula V),

(V)

where $R^1$ has the above mentioned meaning, to give glycosylamines (Formula VI)

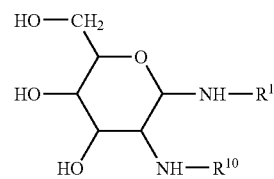
(VI)

Glycosylamine preparations of this type are known in principle (ELLIS, Advances in Carbohydrate Chemistry 10, 95 (1955)) and are, specifically, described in DE-OS (German Published Specification) No. 3,213,650.

In the second reaction step, the glycosylamines (VI) are reacted either with suitable carboxylic acid derivatives (Formula VII), such as carboxyl halides, or carboxylic anhydrides,

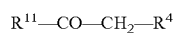
(VII)

$R^2$ having the above mentioned meaning, and $R^{11}$ representing halogen such as, for example, chlorine, or representing —O—CO—$R^2$ with the above mentioned meaning for $R^2$, or representing —O—CO—O-lower alkyl. In this way, glycosylamides (Formula VIII)

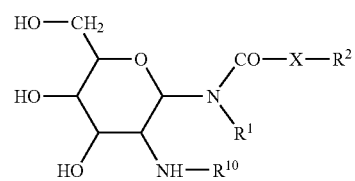
(VIII)

in which $R^1$, and $R^2$ have the above mentioned meanings, and $R^{10}$ is the same as $R^6$ and X represents —$CH_2$—, are obtained. The conditions for N-acylations of this type are indicated in DE-OS (German Published Specification ) No. 3,213,650.

In a preferred embodiment, the glycosylamines of Formula VI are reacted with one to two equivalents of a carbonyl chloride (Formula VII) or with one to two equivalents of a mixed anhydride which has been obtained from the relevant carboxylic acid $R^2$—$CH_2$—$CO_2H$ and ethyl chloroformate or isobutyl chloroformate, in the presence of an organic auxiliary base, by methods known from the literature, to give the glycosylamide of Formula VIII with X=—$CH_2$—.

This is carried out in organic or aqueous-organic solvents between 0° C. and 50° C., where appropriate in the presence of an inorganic or organic base. Suitable diluents are alcohols, such as methanol, ethanol, 1-propanol or 2-propanol, or ethers, such as diethyl ether, tetrahydrofuran or 1,4-dioxane, or halogenated hydrocarbons, such as dichloromethane, trichloromethane or 1,2-dichloroethane, or N,N-dimethylformamide.

When the glycosylamines (VI) which are obtained in the first step are reacted with halogenoformic esters (IX)

(IX)

$R^{12}$ representing halogen such as, for example, chlorine or bromine, and $R^2$ having the above mentioned meaning, then glycosylcarbamates (VIII) are obtained, X in Formula VIII representing oxygen.

In one embodiment, the glycosylamines of Formula VIII are reacted with one to two equivalents of a chlorocarbonic ester IX to give the glycosylcarbamate. This is preferably carried out in organic or aqueous-organic solvents at temperatures between 0° C. and 50° C., but particularly preferably at room temperature. Suitable solvents are alcohols, ethers, halogenated hydrocarbons or dimethylformamide, such as are mentioned above.

When glycosylamines (VI) which are obtained in the first step are reacted with one to two equivalents of an organic isocyanate (Formula X)

$$R^2\text{—NCO} \quad (X)$$

with $R^2$ having the above mentioned meaning, glycosylureas of Formula VIII are obtained, and X is —NH—. This acylation reaction is, like the above mentioned reactions, is preferably carried out in organic solvents, with the reaction temperatures being between −20° C. and 60° C., preferably between 0° C. and 25° C. Suitable solvents are the above mentioned alcohols, ethers, halogenated hydrocarbons, or dimethylformamide.

The glycosylamides (Formula VIII, X=—CH$_2$—), glycosylcarbamates (Formula VIII, X=—O—) or glycosylureas (Formula VIII, X=—NH—) obtained in this way are isolated in the form of crystalline or amorphous solids by processes known per se and, if necessary, are purified by standard procedures such as recrystallization, chromatography, extraction, etc.

In many cases, it is also advantageous to carry out, in parallel with or in place of the above mentioned purification steps, a chemical derivatization which leads to a derivative of the glycosylamides,-carbamates and-ureas of Formula VIII, which has good crystallization properties. Chemical derivatizations of this type are, in the case of the glycosylamides, glycosylcarbamates and glycosylureas according to the invention, for example esterification reactions on the hydroxyl groups of the sugar residues. Examples of suitable ester groups are acetyl, benzoyl or p-nitrobenzoyl groups. To prepare the tri-O-acyl derivatives of the glycosylamides, glycosylureas or glycosylcarbamates, the corresponding triols (Formula VIII) are reacted with acylating agents in the presence of inorganic or organic auxiliary bases. Suitable acylating agents are acid chlorides, such as acetyl chloride, benzoyl chloride or p-nitrobenzyl chloride, or anhydrides, such as, for example, acetic anhydride. This results in the formation of the esters according to Formula XI

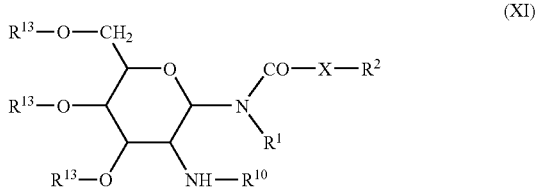

(XI)

with $R^1$, $R^2$, $R^{10}$ and X having the above mentioned meanings, and
$R^{13}$ representing acetyl, benzoyl or p-nitrobenzoyl.

The O-acylation reactions are preferably carried out in inert organic solvents. Those which may be used are halogenated hydrocarbons, such as dichloromethane, trichloromethane or 1,2-dichloroethane, ethers, such as tetrahydrofuran, or 1,4-dioxane, esters, such as ethyl acetate, and amides, such as dimethylformamide. It is also possible for organic bases alone, such as triethylamine or pyridine, to be indicated as suitable solvents. The bases which can be used are all the bases used in organic chemistry for O-acylations. Preferably, triethylamine, pyridine or the mixture pyridine/4-dimethylaminopyridine are used. The triesters (Formula XI) can be readily crystallized from organic solvents. Particularly preferred for the crystallization are polar solvents, such as short-chain alcohols, that is to say methanol, ethanol, n-propanol or isopropanol. Other solvents suitable for the crystallization of the triesters (Formula XI) are mixtures of organic solvents with polar inorganic or organic solvents, for example tetrahydrofuran-methanol, tetrahydrofuran-water, ethanol-water, and isopropanol-water. The triesters (Formula XI) which have been purified by single or, where appropriate, multiple recrystallization are returned to the triols (Formula VIII) by hydrolysis or transesterification of the three O-acetyl groups. A multiplicity of types of ester cleavages are known in organic chemistry. For the preparation of the triols (Formula VIII) from the triesters (Formula XI) mentioned may be made of the transesterification of the acyl groups in the presence of methanol and catalytic amounts of sodium methanolate, which is known as the ZEMPLEN hydrolysis in organic chemistry.

The third reaction step in the preparation of the compounds of Formula I according to the invention comprises the selective cleavage of the protective group of the 2-amino group on the sugar in the compounds of the Formula VIII. In this reaction, particular care has to be taken that there is no simultaneous elimination of the 1-amido or the 1-carbamido or the 1-(alkoxycarbonylamido) group on the sugar in the compounds of the Formula VIII.

The benzyloxycarbonyl group, which is preferably used, on C-2 of the aminohexanes can be quantitatively and selectively cleaved, with retention of the 1-amido, 1-carbamido or 1-alkoxycarbonylamido group, under the conditions of hydrogenolysis. This hydrogenolysis provides the glycosylamides, glycosylureas or glycosylcarbamates with a free 2-amino group on the sugar with the following structural Formula (XII)

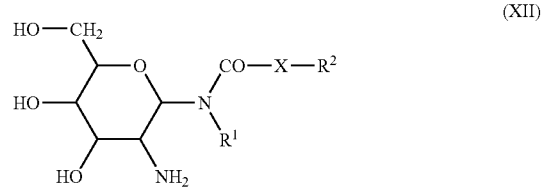

(XII)

with the above mentioned meanings for $R^1$, $R^2$ and X.

Examples of suitable catalysts for the hydrogenolysis are noble metals such as platinum or palladium which are adsorbed onto active charcoal. Palladium/charcoal (5% or 10%) is preferably used. The hydrogenolysis can be carried out under atmospheric pressure or elevated pressure in a suitable pressure vessel, Inert solvents are suitable for the hydrogenation, such as, for example, alcohols such as methanol, ethanol, or propanol, ethers such as tetrahydrofuran or 1,4-dioxane, or carboxylic acids such as acetic acid, or mixtures thereof. Where appropriate, the solvent is mixed with water or dilute acids such as hydrochloric acid or sulphuric acid. Of course. when such acids are added, the 2-amino-2-deoxy-glycosylamides,-carbamates and-ureas according to Formula XII are obtained as the ammonium salts of these acids. The t-butyloxycarbonyl protective group, which is likewise preferably used in the compounds of Formula VIII, can be cleaved by methods known from the literature using mineral acids such as hydrochloric acid or sulphuric acid. In this case too, the 2-amino-2-deoxy-glycosylamides,-carbamates and-ureas of Formula XII are selectively obtained as the ammonium salts of the acids used for the cleavage.

The fourth reaction step for the synthesis of the compounds of Formula I, according to the invention, comprises the linkage of the aminoglycosylamides, amides,-carbamates or-ureas according to Formula XII, or of their salts, with a suitable amino acid derivative. Suitable amino acid derivatives are N-blocked amino acids (Formula XIII)

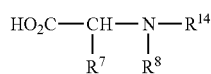
(XIII)

with $R^7$ having the above mentioned meaning, $R^8$ representing hydrogen or methyl,
and $R^{14}$ representing a protective group which is customarily used in peptide synthesis and can be selectively eliminated again while retaining the peptide bond.

The protective groups for the amino group in Formula XIII which are preferably used are the above mentioned, and the benzyloxycarbonyl or t-butyloxycarbonyl groups are particularly preferred. The linkage of the 2-amino-2-deoxy-glycosylamide, -carbamate or- urea of Formula XII with an amino acid derivative of Formula XIII can be carried out by conventional methods of peptide synthesis (E. Wunsch et at.: Synthese von Peptiden (Synthesis of peptides) in: Methoden der Org. Chemie (Methods of org. chemistry) (Houben-Weyl) (E. Muller, Editor), Vol XV/I and XV/2, 4th Edition, published by Thieme, Stuttgart (1974).

Examples of conventional processes are the condensation of the amino group in the compound of Formula XII with an amino acid derivative of Formula XIII in the presence of water-removing agents, for example dicyclohexylcarbodiimide or diisopropylcarbodiimide. The condensation of the compounds of Formula XII with those of Formula XIII can also be carried out when the carboxyl group is activated. A possible activated carboxyl group is, for example, an acid anhydride, preferably a mixed anhydride, such as an acetate of the acid, or an amide of the acid, such as an imidazolide, or an activated ester. Examples of the activated esters are cyanomethyl esters, pentachlorophenyl esters, and N-hydroxyphthalimide esters. Activated esters can also be obtained from the acid (Formula XIII) and N-hydroxysuccinimide or 1-hydroxybenzothiazole in the presence of a water-removing agent, such as carbodiimide. The derivatives of the amino acids are known and can be prepared in a known manner. The condensation of the amino compound of Formula XIII with the optionally activated carboxyl compounds of Formula XIII provides the peptidoglycolipids of Formula XIV.

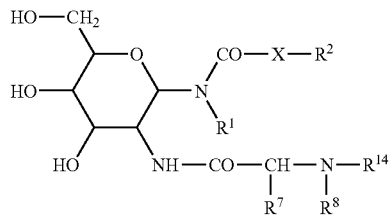
(XIV)

with the above mentioned meanings for $R^1$, $R^2$, $R^7$, $R^8$, $R^{14}$ and X.

In a final process step for the preparation of the compounds according to Formula I, the protective group $R^{14}$ in the compounds of Formula XIV is eliminated. Care has to be taken during this step that the other amide, urethane or urea groups present in the compounds of Formula XIV are not cleaved. The protective groups $R^{14}$ which are preferably used in the compounds of Formula XIV, the N-carbobenzoxy group and the N-tert.-butyloxycarbonyl group, can be eliminated while retaining the amide, urethane or urea group. The carbobenzoxy group can be selectively eliminated by hydrogenolysis in the presence of a noble metal such as, for example, palladium on charcoal, in a suitable solvent such as ethanol, methanol, glacial acetic acid or tetrahydrofuran. The solvents may be used as the pure solvent or combined with one another or with water. The reaction may be carried out under either atmospheric pressure or under elevated pressure. The tert.-butyloxycarbonyl group $R^{14}$ in the compounds of Formula XIV can be eliminated by acidolytic processes. Examples of suitable conditions are the use of hydrogen chloride in suitable solvents such as, for example, glacial acetic acid, diethyl ether, dioxane or ethyl acetate, at room temperature. Processes of this type for the cleavage of the t-butyl carbamates are known in principle. The peptidoglycosylamides, -carbamates and -ureas of Formula I which are obtained in this manner, are isolated in the form of crystalline or amorphous solids, by processes known per se, and are, if necessary, purified by standard methods, such as recrystallization, chromatography, extraction etc.

The compounds according to the invention, of Formula 1, can also be prepared by a second synthetic route with similarly good results. This second synthetic route differs from the first, which is described above, in that the sequence of the linkage of the synthons amino sugar amino acid, amine $R^1$—$NH_2$ and carboxylic acid $R^2$—$CH_2$—$CO_2$—H, or carbonic acid derivative $R_2$—O—CO-halogen, or $R^2$—NCO, with the above mentioned meanings of $R^1$ and $R^2$, is different. In this second route, suitable 2-N-(aminoacyt)aminosugars of Formula XV

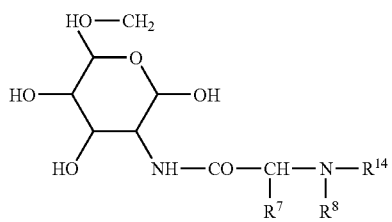
(XV)

with the above mentioned meaning for $R^7$ and $R^8$, and in which $R^{14}$ represents an amino protective group known in peptide chemistry, preferably the benzyloxycarbonyl or the t-butyloxycarbonyl group, are used as the starting component. The compounds of Formula XV which are thus obtained are then condensed with amino compounds of Formula III to give glycosylamines of the general formula XVI

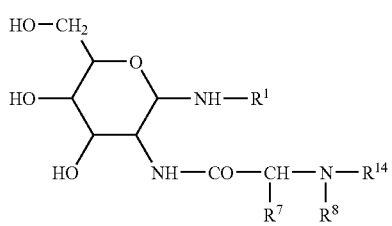
(XVI)

with $R^1$, $R^7$, $R^8$ and $R^{14}$ having meanings consistent with Formula I and the definition of $R^6$.

All the processes described above for the preparation of the compounds of the general Formula VI can be used for the preparation of the compounds of the general Formula XVI. The compounds of Formula XVI are then reacted either with the above mentioned carboxylic acid derivatives (Formula VII) or with halogenoformic esters (Formula IX) or with organic isocyanates (Formula X) to give the 2-(aminoacyl)-aminoglycosylamides of Formula XIV (with X=—CH$_2$—), or the -carbamates of Formula XIV (with X=—O—), or the -ureas of Formula XIV (with X=—NH—). These acylation reactions can generally be carried out by the processes described above for the reaction of glycosylamines with carboxylic or carbonic acid derivatives.

The intermediates (Formula XIV) which are obtained in this way can be purified by the above mentioned physical purification method. However, it is preferable to convert the compounds of Formula XIV, by the methods of O-acylation described above, into the tri-O-acetates or the tri-O-benzoates of the general Formula XVII

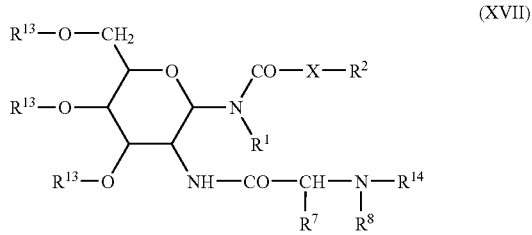

(XVII)

with meaning for the variables consistent with Formula I.

These compounds can readily be crystallized, preferably from polar solvents such as methanol or ethanol, and thus purified. The purified crystalline derivatives of Formula XVII are then converted into the triols of Formula XIV by the above mentioned methods of ester hydrolysis, which are widely used especially in sugar chemistry. The final elimination of the protective groups in the amino acid in the compounds of Formula XIV has already been described above for the preparation of the compounds of Formula I. The invention also relates to salts of the compounds of Formula I. These are primarily the non-toxic salts which can customarily be used in pharmacy, for example chlorides, acetates and lactates, or inert salts of the compounds of Formula I.

The term "weak acid" means any acid having a pKa (the −log of the Ka) value of between about 1.0 and about 9.5 using standard tables or values. While not intending to limit this invention, the following examples of weak acids, are described with name, formula, and approximate pKa: acetic acid, H(C$_2$H$_3$O$_2$) (pKa 4.76); ascorbic acid(l.), H$_2$(C$_6$H$_6$O$_6$) (pKa 4.10); acetylsalicylic acid, H$_8$(C$_9$O$_4$), (pKa 3.5); butanoic acid H(C$_4$H$_7$O$_2$) (pKa 4.83); carbonic acid, H$_2$CO$_3$, (pKa 4.83 form 1); chromic acid, HCrO$_4^-$, (pKa 6.49 form 2); citric acid, H$_3$(C$_6$H$_5$O$_7$), (pKa 3.14 form 1); citric acid, H$_2$C$_6$H$_5$O$_7^-$, (pKa 4.77 form 2); citric acid, (HC$_6$H$_5$O$_7$)$^=$, (pKa 6.39 form 3); formic acid. H(CHO$_2$), (pKa 3.75); fumaric acid, H$_4$(C$_4$O$_4$) (pKa 3.03); heptanoic acid, H(C$_7$H$_{13}$O$_2$), (pKa 4.89); hexanoic acid, H(C$_6$H$_{11}$O$_2$), (pKa 4.84); hyrofluoric acid, HF, (pKa 3.20); isocitrate, H$_8$(C$_6$O$_7$) (pKa 3.29); lactic acid, H(C$_3$H$_5$O$_3$), (pKa 3.08); maleic acid, H$_4$(C$_4$O$_4$) (pKa 1.83); nicotinic acid, H$_5$(C$_6$NO$_2$) (pK3.39); oxalic acid, H$_2$(C$_2$O$_4$), (pKa 1.23 form 1); oxalic acid, (HC$_2$O$_4$)$^-$, (pKa 4.19 form 2); pentanoic acid, H(C$_5$H$_9$O$_2$), (pKa 4.84); phosphoric acid, H$_3$PO$_4$, (pKa 2.16 form 1); propanoic acid, H(C$_3$H$_5$O$_2$), (pKa 4.86); pyruvic acid, H$_4$(C$_3$O$_3$) (pKa 2.39); succinic acid 6(C$_4$O$_4$) (pKa 4.19) and trichloroacetic acid, H(C$_2$C$_{13}$O$_2$) (pKa 0.70). Any combination of any number of these acids are also exemplified.

Acetic acid is preferred. Acetylsalicylic acid, citric acid, formic acid, fumaric acid, hyrofluoric acid, isocitrate, maleic acid, nicotinic acid, phosphoric acid, pyruvic acid, succinic acid and trichloroacetic acid are more common weak acids that are embodied individually, in combination and as a collection.

The term "suitable surfactants" useful for this invention will be both non-ionic and amphiphilic and acceptable for veterinary or medical use. The term "surfactant" means a substance that reduces the surface tension of the material it is dissolved in. The term "non-ionic" means the substance has a polar group that is not electrically charged. The term "amphiphilic" means a substance where a part of the surfactant molecule is hydrophobic and a part is hydrophilic. Whether or not a particular surfactant is acceptable for medical or veterinary use can be readily determined by those of ordinary skill in the art. There are many suitable surfactants that can be used with this invention and numerous examples are provided below. Two well know types of suitable surfactants are embodied here. These are known as sorbitans, commonly sold under the SPAN® trademark, and polyoxyethylene sorbitans, commonly sold under the TWEEN® trademark, Specifically embodied here are the following:

Sorbitan monolaurate (SPAN®20), Sorbitane monopalmitate (SPAN® 40), Sorbitane monostearate (SPAN® 60), Sorbitane tristearate (SPAN® 65), Sorbitane monooleate (SPAN® 80), Sorbitane trioleate (SPAN® 85), Polyoxyethylensorbitan monolaurate (TWEEN® 20), Polyoxyethylensorbitan monopalmitate (TWEEN® 40), Polyoxyethylensorbitan monosterate (TWEEN® 60), Polyoxyethylensorbitan monooleate (TWEEN® 80), and Polyoxyethylensorbitan trioleate (TWEEN® 85). These descriptions are meant to include the trade name ingredients, or equivalent ingredients, as listed in supply catalogues for these surfactants. Surfactants may be used individually or in any combination.

Sorbitan monolaurate (SPAN® 20), Polyoxyethylensorbitan monolaurate (TWEEN® 20), Sorbitane monooleate (SPAN® 80), Sorbitane trioleate (SPAN® 85), Polyoxyethylensorbitan monooleate (TWEEN® 80), Polyoxyethylensorbitan trioleate (TWEEN® 85) are particularly described.

The term "suitable buffer" means a buffer that is suitable for veterinary or medical use and can maintain a relatively constant pH in an aqueous solution of between about 6 and about 8. Phoshpate buffers are one embodiment described here. Phosphate buffers can be made at a specific pH in a wide range by means of mixing monobasic and dibasic salts of sodium phosphate and/or potassium phosphate at different proportions. The making and use of various sodium and potassium buffers is well known to one skilled in the art.

Other examples of buffers are as follows:

2-(N-morpholino)ethanesulfonic acid (also known as MES);

3-(N-morpholino)propanesulfonic acid (also known as MOPS);

n-[tris(hydroxymethyl]-2-aminoethanesulfonic acid (also known as TES);

4-(2-hydroxyethyl)piperazine-1-ethanesulfonic acid (also known as HEPES);

[tris(hydroxymethyl)methyl]glycine (also known as TRIS).

Part 1. Preparation of the Solutions

The novel formulations disclosed here are 1) Glycosylamide Stock Solutions and 2) Glycolipid Adjuvant Solutions.

1) A Glycosylamide Stock Solution is prepared by dissolving a glycolipid in an alcohol and combining appropriate amounts of a weak acid. The weak acid is added to the glycolipid alcohol solution, in molar excess of the weak acid with reference to the glycolipid. A non-ionic surfactant is added to the glycolipid alcohol acid mixture to create a Glycosylamide Stock Solution. The glycolipid exemplified is N-(2-deoxy-2-L-leucylamino-β-D-gulucopyranosyl)-N-octadecyldodecanoylamide acetate. The alcohol exemplified is ethanol. The weak acid exemplified is acetic acid. The non-ionic surfactants are as described above.

Preparation of CGlycosylamide Stock Solutions. Weak acid is added to an alcoholic solution containing a glycolipid. The weak acid is added in molar excess with reference to the glycolipid content, The weak acid component should preferably be added from 1.25 to 5 times the amount of the glycolipid, as measured in molar equivalents to the glycolipid. In certain embodiments the following relative amounts of acid are recommended. The weak acid should be 2.0 times, 2.5 times, 2.7 times, 3.0 times, and 5.0 times, and most preferred is 2.7 times as many moles of acid as moles of glycolipid.

A non-ionic surfactant is added to the alcohol glycolipid mixture, either before or after the weak acid is added, to create the Glycosylamide Stock solution.

In the presence of the weak acid, the glycosylamide is converted into the acetate form of the glycolipid. The glycolipids of Formula I are not fully soluble when simply introduced directly into buffered aqueous solutions. The solution typically obtained from dissolving a glycolipid of Formula I into a buffered aqueous solution is a milky mixture. Earlier researchers have attempted to make such solutions of mixtures homogenous by means of sonicating the milky solution. However, sonication does not assure the solution will remain homogeneous during storage. The chemical approach to suspending these compounds described here results in a fully soluble, nearly optically clear solution, of aqueous buffered glycolipid, at appropriate pH. When weak acid is added in excess amount compared to the glycolipid it ensures that all the glycolipid is converted into a soluble form, and its reversion back to non-soluble form is prevented.

The weak acid converts the glycolipid into a pharmaceutically acceptable salt. Preferred salts are non-toxic salts, which are customarily used in pharmaceutical and biological preparations. For example, chlorides, acetates, lactates, and inert salts of the compounds of Formula I, are obtained with the weak acids described herein.

The alcohols used to dissolve the glycolipid may be methanol, ethanol, any isomeric form of propanol, or any combination thereof. The resulting glycolipid alcohol solution will be optically clear. Any chemical reaction that could convert the acetate form of glycolipid back to non-acetate form would cause flocculation of the glycolipids within the aqueous solution. When the flocculation of glycolipid occurs, the glycolipid molecules come out of solution as thin flakes, settling at the bottom of the container. The initial concentration of weak acid in the Glycosylamide Stock Solution of glycolipid and alcohol determines whether there will be any flocculation of glycolipid. The weak acid should be in molar excess with reference to the glycolipid to avoid flocculation.

2) Glycolipid Adjuvant Solutions are prepared by introducing an appropriate amount of the Glycosylamide Stock Solution into a "suitable buffer." The pH of the final stable Glycolipid Adjuvant Solutions described here should be between about 6 and about 8. A final pH of between about 6 to about 7 is preferred. A final pH of between about 6.3 to about 6.4 is described.

The Glycosylamide Stock Solution contains excess acid so it should be buffered for use as an adjuvant. For example, a phosphate buffer can be made at a specific pH in a wide range by means of mixing monobasic and dibasic salts of sodium phosphate or potassium phosphate at different proportions. If a phosphate buffer is used it can be made at about 20 mM, and this has a pH of about 7.8. When the Glycosylamide Stock Solution is added to the buffer, the pH of the buffer is lowered.

A phosphate buffered solution at pH 7.8 results in a Glycolipid Adjuvant Solution with a pH of about 6.4. Final pH adjustments may be made but are typically not necessary.

The Glycosylamide Stock Solution containing weak acid and a glycolipid has a very low pH. It may be necessary to raise the pH to an acceptable level. A strong base should be avoided for this purpose because addition of a strong base can convert the salt form of the glycolipid back to the non-salt form, resulting in precipitation (flocculation) of the non-salt form in the aqueous environment. However, if a strong base is desired, only small amounts should be used. For example, it is recommended that no more than 100 mM NaOH be used, while 4.0 mM or less is optimal.

The buffering solution may optionally include some NaCl, but it is not required. NaCl concentrations can range from about 1 to about 50 mM. Lower amounts of NaCl are preferred over greater amounts. Examples here have either no NaCl or 15 mM NaCl. 100 mM NaCl is not suitable as flocculation occurs. No flocculation is expected with NaCl concentrations of 15 mM or less. No flocculation is expected with NaCl concentrations of 30 mM or less. No flocculation is expected with NaCl concentrations of 50 mM or less.

Part II. Characterization of the Glycolipid Adjuvant Solution

The stability of the Glycolipid Adjuvant Solution during storage may be monitored by simple visual observation or by using appropriate analytical instruments. Glycolipid molecules form micelles when in aqueous solution and it is possible to determine the size of the micelles precisely with a laser diffractometer. Such a measurement can be used to determine whether there is flocculation of glycolipid molecules.

An alternative approach to real time stability measurement is to perform accelerated stability testing. With accelerated stability testing the adjuvant solution is subjected to a temperature of about 37° C. for about seven days, followed by incubation at about 4° C. for about two days under constant shaking. The incubation at about 37° C. for about seven days represents the storage at about 4° C. for a period of about one year. The incubation at about 4° C. for about two days with constant shaking represents the stress condition the Glycolipid Adjuvant Solution could face during transportation.

To determine whether the Glycolipid Adjuvant Solution is isotonic with the cytoplasm, the osmolarity can be determined. Different concentrations of sodium chloride can be added and the osmolarity of the resulting solution determined using an osmometer. Increasing concentrations of sodium chloride, besides increasing the osmolarity, also tend to make the solution more turbid. Turbidity is thought to be caused by aggregation of micelles into larger particles. Solutions that are difficult or impossible to filter using a 0.2 μm filter are generally not acceptable for commercial use because terminal filtration is often used to assure the sterility of adjuvant solutions prepared on a commercial scale. An electron microscopic analysis can be used to determine whether there is an aggregation of micelles as a result of too much salt.

Additional non-glycolipid adjuvants may be used in the Glycolipid Adjuvant Solution in combination with those described above. In another embodiment of the invention, additional immunostimulatory molecules are added to the Glycolipid Adjuvant Solution. Immunostimulatory molecules are well known in the art, and they include saponins, Quil A, dimethyl dioctadecyl ammonium bromide (DDA) and Carbopol.

Quil A is a purified extract from the bark of the South American tree *Quillaja saponaria*. Quil A induces both humoral and cell-mediated responses. Quil A is often used with cholesterol because cholesterol eliminates less desirable side effects when added in the appropriate proportions. Cholesterol forms insoluble complexes with Quil A that form helix-like structures as the cholesterol binds with Quil A, thus exposing the molecule's sugar units that help stimulate the immune response.

Dimethyl dioctadecyl ammonium bromide, DDA, is a cationic surfactant with 18 carbon alkyl chains. It is an amphiphilic quaternary amine. Direct interaction of DDA and antigen is needed to obtain an optimal immune response, because DDA functions as a carrier of antigen through direct binding of the antigen at the oil/water interface. It stimulates both the humoral and the cell-mediated immune responses.

Carbopol is another useful immunostimulatory molecule that may be used with this invention. It is an acrylic acid homopolymer that is cross-linked with polyalkenyl ether.

Part III. Uses of the Glycolipid Adjuvant Solution

The Glycolipid Adjuvant Solution, in a pharmaceutically acceptable salt form, can be mixed with an antigen. Convenient antigens include: microbial pathogens proteins, glycoproteins, lipoproteins, peptides, glycopeptides, lipopeptides, toxoids, carbohydrates, and tumor specific antigens. The antigens can be derived from a variety of sources. Antigens from microbial pathogens include disease causing bacteria, viruses. and parasitic organisms. Mixtures of two or more antigens may be employed. The antigen may be killed, naturally attenuated, modified live, or a protein extract, recombinantly produced protein, a chemically synthesized peptide or anything else that stimulates an immune response. The pptide antigen may exist as a free peptide or conjugated to the glycolipid or conjugated to other known B-cell or T-Cell epitopes.

The stable Glycolipid Adjuvant Solution can be combined with additional adjuvants or components which are known to have adjuvant properties. Additional adjuvants that can be combined with the Glycolipid Adjuvant Solution include polymers, naturally occurring terpenoid compounds in their crude or partially purified form, amphiphilic quaternary amine, derivatives of bacterial cell wall materials and synthetic analogues of bacterial cell wall or DNA components. The Glycolipid Adjuvant Solution may be used with or combined with one or more agents such as antibiotics or different antigens. Bacterial or viral antigens may either be killed or modified live. Killed viral antigens are prepared by growing viruses in tissue culture and inactivating the viruses through chemical treatments. Some viruses can be grown in embroynated eggs. The killed viral antigen can be added to solution containing Glycolipid Adjuvant Solution, and the resulting solution can be used to vaccinate the animals to achieve protection against the viral infections.

In one embodiment of this invention, the Glycolipid Adjuvant Solution can be used as a diluent for modified live viral antigens. Viral pathogens can be attenuated in their virulence either by passing them in tissue culture for several generations or through specific manipulations of the viral genome. Such attenuated strains of viruses can be grown to very high titers in tissue culture and can be used as vaccine antigens. Attenuated viral strains are referred to as modified live viral antigens. While these strains are less virulent, they are still highly immunogenic when used as antigen in the vaccine and offer protection against the infection by virulent strains. Should the Glycolipid Adjuvant Solution be used as a diluent for modified live viral antigens, the Glycolipid Adjuvant Solution should be tested to ensure it does not have any viricidal effect on the particular virus of interest.

The viricidal property of the Glycolipid Adjuvant Solution on modified live viral antigens can be determined in an in vitro experiment. Lyophilized viral antigens are rehydrated with the Glycolipid Adjuvant Solution or with water. The resulting virus solutions are plated on a monolayer of permissive cells. The titer of the viral antigen is determined by means of counting the number of plaques formed on the monolayer. The difference in the viral titers obtained between the samples rehydrated with water and the Glycolipid Adjuvant Solution can be used to determine what, if any, viricidal effect of the Glycolipid Adjuvant Solution on any live virus.

Modified live viral antigens may be lyophilized and provided as lyophilized cakes in a commercial vaccine preparation In general, these lyophilized cakes of modified live viral antigens are rehydrated with a diluent solution and used for parenteral vaccination. Examples of diluents include a water solution containing phosphate buffered saline If the diluent solution contains a known immunostimulatory molecule, the efficiency of vaccination with the modified live viral antigens can be improved. In one embodiment of the present invention, the Glycolipid Adjuvant Solution is used as a diluent solution.

EXAMPLES

Example 1

Preparation of an insoluble glycosylamide composition with equal concentration of BAY 15-5831® and acetic acid.

TABLE 1

A composition not suitable for commercial use.

| Reagent | Amount (200 ml) |
| --- | --- |
| Ethanol (100%) | 176.1 ml |
| TWEEN ® 20 | 4.0 ml |
| Glacial Acetic acid | 1.5 ml |
| BAY 15-5831 ® | 18.4 gm |

BAY 15-5831® is registered to the Bayer Company, is the trade name for N- (2-deoxy-2-L-leucylamino-β-D-guluopyranosyl)-N-octadecytdodecanoylamide. When this compound is used to make an adjuvant solution using the compositions described in Table 1, above, where the acetic acid is used in equal molar concentration to the glycolipid, and the glycolipid is in its free base form, the glycolipid is insoluble and flocculates.

Example 2

A Soluble Glycosylamide Stock Solution using the same components as Example 1, but with an increase in the acetic acid concentration relative to the concentration of glycolipd, results in a soluble Glycosylamide Stock Solution.

TABLE 2

Composition of a Glycosylamide Stock Solution.

| Reagent | Amount (50 ml) |
| --- | --- |
| Ethanol (60% v/vol) | 44.64 ml |
| TWEEN ® 20 | 1.12 ml |
| Glacial Acetic acid | 0.68 ml |
| BAY 15-5831 ® | 3.49 gm |

Here, 60% ethanol (v/v) was used, and the molar ratio of acetic acid to glycolipid is 2.0. The 200-proof ethanol of Example 1 was replaced with 60% ethanol water. The resulting Glycosylamide Stock Solution was optically clear and there was no sedimentation at the bottom of the container. This Glycosylamide Stock Solution is added to various buffers to make a Glycolipid Adjuvant Solution in Example 3, below.

Example 3

Preparation of Glycolipid Adjuvant Solutions. Phosphate buffer solutions at different pH were prepared. A 2 M stock of monobasic sodium phosphate solution was prepared by dissolving 138 grams of $NaH_2PO_4 \cdot H_2O$ salt in 250 mL of DI water in a beaker and making the final volume to 500 mL. Similarly a 2M stock of dibasic sodium phosphate solution was prepared by dissolving 142 grams of $NaH_2PO_4$ in 300 mL of DI water in a beaker and making the final volume to 500 mL. Both stock solutions were sterile filtered using a 0.2 mnicron filter.

TABLE 3

Compositions of 1M stock solution of sodium phosphate buffer solution at different pH.

| Calculated pH | $Na_2HPO_4$ Solution (ml) | $NaH_2PO_4 \cdot H_2O$ Solution (ml) | Total Volume of 2M stock solution (ml) | Sterile DI water (ml) added | Total volume of 1M stock solution (ml) |
|---|---|---|---|---|---|
| 6.0 | 87.7 | 12.3 | 100 | 100 | 200 |
| 6.5 | 68.5 | 31.5 | 100 | 100 | 200 |
| 7.0 | 39.0 | 61.0 | 100 | 100 | 200 |
| 7.5 | 16.0 | 84.0 | 100 | 100 | 200 |
| 7.8 | 8.5 | 91.5 | 100 | 100 | 200 |

Different volumes of 2M stock of monobasic sodium phosphate and dibasic sodium phosphate solutions as shown in Table 3 were prepared, then 1M stock solution of sodium phosphate buffer solutions were obtained at a different pH levels. The 1M phosphate buffer solutions were then diluted 50× to get 20 mM phosphate buffers.

Glycolipid Adjuvant Solutions were prepared using these stock buffers and the Glycosylamide Stock Solutions from Example 2.

To 96 mL of each of these 20 mM phosphate solutions, 5 mL of Glycosylamide Stock Solution as prepared in Example 2 was added. The resulting Glycolipid Adjuvant Solution contained 12.5 mM acetic acid and 6.33 mM glycolipid. The glycolipid is now in the acetate form.

Example 4

Significance of the final pH of the Glycolipid Adjuvant Solution.

In another set of experiments, the significance of the final pH of various solutions was tested to evaluate how pH affects flocculation. A 20 mM phosphate buffer was prepared at an initial pH of 7.8. Table 4 shows the adjuvant prepared using the glycosylamide prepared as in Example 1, where glycolipid and acetic acid were used in equal molar concentrations. Note. the final pH did not drop very much (Table 4), indicating the effectiveness of the buffer. NaCl concentrations varied. The optical density readings (O.D.) at 600 nm, in Table 4 were compared to similar readings in Table 5, where the Glycolipid Adjuvant Solutions were prepared with Glycosylamide Stock Solutions containing twice the molar ratio of acetic acid to glycolipid, as prepared in Example 2. Using the greater concentration or amount of acetic acid results in minimal flocculation. The flocculation was higher in the non-filtered sample than in the filtered samples. Moreover, with increasing NaCl concentration, there is an increase in flocculation and even precipitation. The Glycolipid Adjuvant Solution described in Table 5 was prepared with a phosphate buffer having an initial pH of 8.0; the final pH of the Glycolipid Adjuvant Solution was between 6.8 and 7.0. A further decrease in the final pH of the Glycolipid Adjuvant Solution may result in a Glycolipid Adjuvant Solution with less turbidity and no flocculation.

TABLE 4

Preparation of glycosytamide compositions containing equimolar amount of acetic acid and glycolipids. (See Example 1.)

| NaCl Concentration (mM) | Volume of buffer (ml) | Volume of Glycolipid Stock compositions (ml) | Final pH | O.D. at 600 nm |
|---|---|---|---|---|
| 0 | 480 | 25 | 7.42 | 1.693 |
| 15 | 480 | 25 | 7.39 | 1.873 |
| 100 | 480 | 25 | 7.33 | 2.742 |

TABLE 5

Preparation of Glycolipid Adjuvant Solution using Glycosylamide Stock Solution containing twice the molar amount of acetic acid as glycolipid. (See Example 2 for Glycosylamide Stock preparation used here.)

| NaCl Concentration (mM) | Volume of buffer (ml) | Volume of Glycosylamide Stock Solution (ml) | Final pH | O.D. at 600 nm |
|---|---|---|---|---|
| 0 | 480 | 25 | 6.93 | 0.146 |
| 15 | 480 | 25 | 6.88 | 0.487 |
| 100 | 480 | 25 | 6.84 | 2.826 |

An optical density (O.D). of less than 0.1 represents a translucent solution. An optical density of between 0.1 and 0.5 is homogeneous with slight turbidity, an optical density of 0.5 to 1.0 has some turbidity, an optical density of 1.0 to 1.5 is considered turbid. An optical density over 1.5 is turbid and not likely to be filterable using a 0.2 micron filter. The latter would generally not be considered commercially suitable.

Example 5

Titration of glycolipid adjuvant with acetic acid to show flocculation can be reversed. To determine whether adding increasing amount of acetic acid to the glycolipid djuvant showing flocculation would reverse the flocculation, a glycolipid adjuvant as described in Example 1 was prepared. This glycolipid adjuvant showed flocculation even in the absence of any NaCl. An increasing concentration of acetic acid was added to this flocculated glycolipid adjuvant mixture. The acetic acid was diluted 16.6 times with water to get a working solution concentration of 1 Molar. Then 15 µl of this 1M solution was added to 15 ml of glycolipid adjuvant mixture to increase the acetic acid concentration by 1 mM. With increasing concentration of acetic acid, the pH of the glycolipid adjuvant decreased and the flocculates dissolved. However, the glycolipid adjuvant remained somewhat turbid. This observation confirms that increasing acetic acid concentration converts the free base of BAY 15-5381® into an acetate form, which is more soluble in aqueous solution.

TABLE 7

Titration of Glycolipid Adjuvant with acetic acid.

| Volume of Glycolipid Adjuvant | Volume of 1N Acetic Acid added | pH of the Solution |
|---|---|---|
| 15 mL | 0 | 7.25 |
| 15 mL | 15 µl (1 mM) | 7.21 |
| 15 mL | 30 µl (2 mM) | 7.10 |
| 15 mL | 60 µl (4 mM) | 6.97 |
| 15 mL | 150 µl (10 mM) | 6.44 |
| 15 mL | 750 µl (50 mM) | 4.57 |

Example 6

Preparation of a second stable Glycolipid Adjuvant Solution with and without NaCl. After establishing the importance of an increase in the amount of acetic acid in maintaining the stability of glycolipid solutions, it was decided to use the composition shown in Table 8 to first prepare a Glycosylamide Stock Solution and then use this to prepare another Glycolipid Adjuvant Solution both with and without NaCl. This Glycosylamide Stock Solution is similar to the solution in Example 2, with 4 times the total volume and relatively greater amounts of acetic acid and TWEEN® 20.

TABLE 8

Composition of a Glycosylamide Stock Solution.

| Reagent | Amount (200 ml) |
|---|---|
| 60% Ethanol (v/v) | 179 ml |
| TWEEN® 20 | 4.0 ml |
| Acetic acid | 3.0 ml |
| BAY 15-5831® | 13.96 grams |

Three different Glycolipid Adjuvant Solutions with varying concentrations of NaCl were prepared using the phosphate buffer from Example 3 and the Glycosylamide Stock Solution prepared as in Table 8.

Like the formulation in Example 4, Table 5, the Glycolipid Adjuvant Solution was made that contained 0 mM, 15 mM, and 100 mM NaCl. The 0 mM and 15 mM NaCl solutions could be filtered through a 0.2-micron filter. The Glycolipid Adjuvant Solution containing 100 mM NaCl could not be filtered though a 0.2-micron filter.

TABLE 9

Preparation of stable Glycolipid Adjuvant Solutions with and without NaCl.

| Sodium chloride Concentration (mM) | Volume of buffer (ml) | Volume of Glycosylamide Stock solution (ml) | Final pH | O.D. at 600 nm |
|---|---|---|---|---|
| 0 | 465 | 35 | 6.39 | 0.039 |
| 15 | 465 | 35 | 6.37 | 0.073 |
| 100 | 465 | 35 | 6.29 | 0.439 |

20 mL of each of the Glycolipid Adjuvant Solutions were placed into 30 ml glass vials and incubated at room temperature and at 4° C. Visual observations were made on a regular interval. Initially the Glycolipid Adjuvant Solution with 0 mM NaCl was optically clear. The Glycolipid Adjuvant Solution containing 15 mM NaCl was slightly turbid and had an O.D. of 0.073 at 600 nm. The Glycolipid Adjuvant Solution containing 100 mM NaCl was turbid and had an O.D. of 0.439 at 600 nm. Table 9. None of these Glycolipid Adjuvant Solutions showed any signs of flocculation both at room temperature and at 4° C. These Glycolipid Adjuvant Solutions were observed for a period of one year with no change in appearance.

Example 7

Titration of a Stable Glycolipid Adjuvant Solution with NaOH

Initially an optically clear and stable Glycolipid Adjuvant Solution was obtained without NaOH. In order to establish that the elimination or use of a minimal amount of NaOH was essential to prevent flocculation, it is necessary to show that a gradual addition of NaOH would induce flocculation in an otherwise stable glycolipid mixture. Appropriate volumes of 1 N NaOHt were added to 15 mL of Glycolipid Adjuvant Solution without any added NaCl, as prepared in Table 10, below. The NaOH was increased gradually from 1 mM to 12 mM. (Table 10) The Glycolipid Adjuvant Solution used in this experiment was prepared using the Glycosylamide Stock Solution described in Example 6. With increasing concentration of NaOH in the Glycolipid Adjuvant Solution, the pH of the formulation gradually increased along with the appearance of flocculation.

TABLE 10

Titration of a stable Glycolipid Adjuvant Solution with NaOH.

| Volume of Glycolipid Adjuvant | Volume of 1N NaOH Added (mM) | pH of the Solution |
|---|---|---|
| 15 ml | 0 | 6.21 |
| 15 ml | 15 µl (1 mM) | 6.38 |
| 15 ml | 30 µl (2 mM) | 6.48 |
| 15 ml | 60 µl (4 mM) | 6.68 |
| 15 ml | 150 µl (10 mM) | 7.11 |
| 15 ml | 750 µl (50 mM) | 12.17 |

Example 8

Quantification of the glycolipid component using HPLC.

The following methodology was used in the HPLC analysis of BAY 15-5831®. The HPLC parameters described in the Table 11 were used.

TABLE 11

Summary of parameters used in HPLC method for quantifying BAY 15-5831®.

| Parameter | Details |
|---|---|
| Column | Hamilton PRP-1, 7 micron, 250 × 4.6 mm |
| Flow | 1.5 ml/min |
| Injection Volume | 10 µl |
| Detector Wavelength | 210 nm |
| Mobile Phase A | 0.4% perchloric acid, v:v |
| Mobile Phase B | Acetonitrile |
| Gradient | 0 min 40% A/60% B |
|  | 15 min 30% A/70% B |
|  | 20 min 30% A/70% B |
|  | 35 min 10% A/90% B |
|  | 50 min 10% A/90% B |
|  | 51 min 40% A |
| Run time | 65 min |
| BAY 15-5831® retention time | Approximately 25 minutes |

TABLE 12

Standards of BAY 15-5831®.

| Standard | Concentration |
|---|---|
| 1 | 0.103 mM |
| 2 | 0.206 mM |
| 3 | 0.412 mM |
| 4 | 0.618 mM |
| 5 | 0.824 mM |
| 6 | 1.03 mM |

Standards in the range of 0.10 to 1.03 mM were prepared and injected into an HPLC. A summary of the standards is shown in Table 12. Samples were warmed to room temperature and inverted 5 times before using. One ml of sample was added to 6 ml of methanol in a 10 ml volumetric flask. Samples were then sonicated for 10 minutes and then diluted to volume and mixed. Linear regression was performed on the standards with peak areas plotted against concentration. The samples were then calculated against the curve.

Example 9

Thirty (30) liter scale production. A 30 Liter batch of Glycolipid Adjuvant Solution with a compsition as described in Example 6 was prepared. This batch contained 15 mM NaCl.

Using this 30 L preparation, five different sub-solutions were prepared with increasing concentration of NaOH. The NaOH concentration increased from 0 mM to 1 mM, 2 mM, 4 mM, 8 mM, and 12 mM. The sample for each NaOH concentration was aliquoted for pH measurement and visual observation. With increasing amounts of NaOH, the pH of the glycolipid adjuvant increased along with increased flocculation. The flocculation started to appear at 2 mM NaOH concentration at room temperature, and at 4° C., the flocculation started to appear at 4 mM NaOH.

TABLE 13

Characteristics of 30-L batch glycolipid adjuvant with increasing concentration of NaOH.

| Sample No. | Description | Measured Concentration (mM) | O.D. at 600 nM | pH |
|---|---|---|---|---|
| 30-L Sample 1 | 15 mM NaCl, 0 mM NaOH | 6.21 | 0.218 | 6.42 |
| 30-L Sample 2 | 15 mM NaCl, 1 mM NaOH | 6.3 | 0.137 | 6.52 |
| 30-L Sample 3 | 15 mM NaCl, 2 mM NaOH | 6.24 | 0.137 | 6.59 |
| 30-L Sample 4 | 15 mM NaCl, 4 mM NaOH | 6.17 | 0.15 | 6.80 |
| 30-L Sample 5 | 15 mM NaCl, 8 mM NaOH | 6.26 | 0.129 | 7.06 |
| 30-L Sample 6 | 15 mM NaCl, 12 mM NaOH | 6.15 | 0.062 | 7.54 |

The amount of BAY 15-5381® in all the six samples shown in the Table 13 was quantified using HPLC method described in Example 8. The samples with varying pH showed the same concentration of BAY 15-5381® suggesting that the adjuvant component is not degraded during the pH increase with the addition of NaOH and accompanying flocculation.

Example 10

Stability evaluations using accelerated stress testing. This example describes the methods and results of accelerated stress testing on the Glycolipid Adjuvant Solution. Three batches of Glycolipid Adjuvant Solutions as described in Example 6 were prepared at the 500 L scale. All three batches had 15 mM NaCl and contained no NaOH. The Glycolipid Adjuvant Solutions from these three 500 L batches were used for studying the stability of the glycolipid using an accelerated stability testing.

For accelerated stress testing, the Glycolipid Adjuvant Solution was subjected to shaking for seven days at 37° C., followed by shaking at 4° C. for two days. The seven days of shaking at 37° C. represents aging at 4° C. for a year. The shaking at 4° C. for two days represents stress during transportation.

One set of Glycolipid Adjuvant Solution was kept static at 37° C. for 7 days, then shaken at 100 rpm at 4° C. for an additional 2 days. At four time points, i.e. TeO, 3, 7, and 9 days, observation and photo picture were recorded. At 2 time points, i.e. T=0 and 9 days, Refractive Index and particle size analysis were then performed.

The second set of Glycolipid Adjuvant Solution was shaken at 100 rpm at 37° C. for 7 days; then shaken at 100 rpm at 4° C. for an additional 2 days. At four time points, i.e. T=0, 3, 7, and 9 days, observation and photo picture were recorded. At 2 time points, i.e. T=0 and 9 days, Refractive Index and particle size analysis were then performed.

The third set of Glycolipid Adjuvant Solution was static at 4° C. for 9 days as control. At four time points, i.e. T=0, 3, 7, and 9 days, observation and photo picture were recorded. At 2 time points, i.e. T=0 and 9 days, Refractive Index and particle size analysis were then performed.

There was no change in the particle size as the result of stress testing. All the samples maintained sub-micron particle size as observed in the samples immediately after it was prepared. Moreover, a HPLC measurement of BAY 15-5831® component in the samples kept at 4° C. or subjected to stress at 37° C. for seven days did not show any change in the amount of BAY 15-5831®.

TABLE 15

Quantification of Bay 15-5831 ® after stress testing.

| Batch number of the Glycolipid Adjuvant Solution and treatment | Measured concentration (mM) |
|---|---|
| Batch 1 - 4° C. | 6.23 |
| Batch 1 - 37° C. Shaking | 6.29 |
| Batch 2 - 4° C. | 6.32 |
| Batch 2 - 37° C. Shaking | 6.30 |
| Batch 3 - 4° C. | 6.28 |
| Batch 3 - 37° C. Shaking | 6.29 |

In Table 15, the control samples were kept at 4° C. for seven days, while the test samples were shaken at 37° C. for seven days. The samples shaken at 37° C. for seven days have concentrations similar to those stored at 4° C.

Example 11

Viricidal testing of the Glycolipid Adjuvant Solution

Viricidal testing was conducted on the Glycolipid Adjuvant Solution prepared in a 30 L scale as described above in Example 9. This Glycolipid Adjuvant Solution contained 15 mM NaCl and no NaOH.

The glycolipid adjuvant was tested for its suitability to use it as a diluent with modified live viruses. Modified live viral antigens are prepared as freeze dried plugs. Upon rehydration of these plugs with suitable Glycolipid Adjuvant Solution, it was confirmed that the Glycolipid Adjuvant Solution used does not kill the modified live viruses. The Glycolipid Adjuvant Solution was tested against three bovine viral antigens: Bovine Respiratory Synctial virus (BRSV), Para-influenza Virus 3 (PI3), and Infectious Bovine Rhinotrachetis (fBR) virus.

Viral plugs were rehydrated using the Glycolipid Adjuvant Solution. After incubation at room temperature (RT) for 1 hour, the samples were plated on a monolayer of a permissive cell line with a serial dilution. By counting the number of viral plugs that appear on the monolayer, the 50% tissue culture infective dose per ml (TCID50/ml) value was obtained for each viral antigen rehydrated with sterile water or Glycolipid Adjuvant Solution. In this assay, a decrease in the titer of 0.7 after rehydrating with the test Glycolipid Adjuvant Solution was treated as viricidal.

The results are presented in Table 16. Glycolipid Adjuvant Solution did not show any viricidal effect on these three bovine viruses.

TABLE 16

| Viricidal assay for Glycolipid Adjuvant Solution. | | | | |
|---|---|---|---|---|
| Virus | Original titer | Final titer with Glycolipid Adjuvant | Final titer with sterile water | Loss in the titier |
| tsIBR 051404 | 7.3 ± 0.5 | 7.08 | 7.49 | 0.42 |
| tsPI3 052604 | 7.6 ± 0.5 | 7.74 | 7.49 | −0.25 |
| BRSV 081103 | 6.4 ± 0.5 | 6.57 | 6.82 | 0.25 |

This example shows the Glycolipid Adjuvant Solution may be used in a commercial formul ation of an Animal Health vaccine. Rispoval® contains three different bovine viral diseases using 3 modified live viral antigens. These bovine viral antigens are modified live bovine herpes virus, modified live bovine respiratory synctial virus, and modified live parainfluenza virus 3. These viral antigens are produced as a lyophilized cakes and the Glycolipid Adjuvant Solution produced by this invention can be used as diluent solution for these antigens. The glycolipid used was N-(2-deoxy-2-L-leucylamino-β-D-glucopyranosyl)-N-octadecyldodecanamide acetate.

The examples are presented to illustrate the invention. They should not be taken as limiting the scope of the invention. Many changes, variations, modifications, and other uses and applications of this invention will be apparent to those skilled in the art.

What is claimed is:

1. A composition comprising:

a) a glycolipid of Formula I;

wherein Formula I is 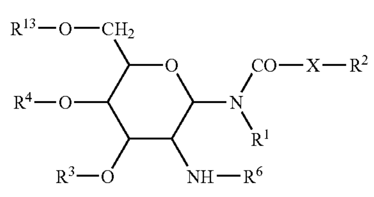 wherein $R^1$ is hydrogen, or a saturated alkyl radical having up to 20 carbon atoms;

X is —$CH_2$—, —O— or —NH—;

$R^2$ is hydrogen, or a saturated or unsaturated alkyl radical having up to 20 carbon atoms;

$R^3$, $R^4$, and $R^5$ are independently hydrogen, —$SO_4^{2-}$, —$PO_4^{2-}$, or —$COC_{1-10}$alkyl;

$R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L -methionyl, L-ornithinyl, L-phenylalanyl; L-prolyl, L-seryl, L-threonyl, L-tyrosyl, L -tryptophanyl, or L-valyl, or their D-isomers;

in a salt form, where the salt form is derived from a weak acid, b) an alcohol, wherein the alcohol is HO—$C_{1-3}$ alkyl;

c) a weak acid, wherein the weak acid is, 1) in molar excess with reference to the glycolipid content, and 2) any acid having a pKa (the −log of the Ka) value of between 1.0 and 9.5;

d) a non-ionic surfactant, where the non-ionic surfactant is an agent that reduces the surface tension of the material it is dissolved in and has a component that is hydrophobic and another component that is hydrophilic;

further wherein the composition is stable for up to one year, shows little or no flocculation for up to one year, has a pH from about 6 to about 8, and has an optical density of about 1.0 or less.

2. A composition of claim 1 wherein the glycolipid is a compound of Formula II(a)

Formula II(a)

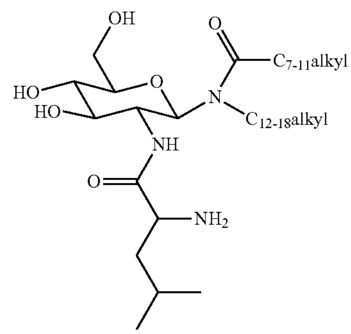

and the weak acid is selected from one or any combination of the following weak acids: acetic acid, $H(C_2H_3O_2)$ (pKa 4.76); ascorbic acid(1), $H_2(C_6H_6O_6)$ (pKa 4.10); acetylsalicylic acid, $H_8(C_9O_4)$, (pKa 3.5); butanoic acid $H(C_4H_7O_2)$ (pKa 4.83); carbonic acid, form 1, $H_2CO_3$, (pKa 4.83); chromic acid, form 2, $HCrO_4^{-1}$ (pKa 6.49); citric acid form 1, $H_3(C_6H_5O_7)$, (pKa 3.14); citric acid form 2, $H_2C_6H_5O_7)^-$, (pKa 4.77); citric acid form 3, $(HC_6H_5O_7)^=$, (pKa 6.39); formic acid, $H(CHO_2)$, (pKa 3.75); fumaric acid, $H_4(C_4O_4)$ (pKa 3.03); heptanoic acid, $H(C_7H_{13}O_2)$, (pKa 4.89); hexanoic acid, $H(C_6H_{11}O_2)$, (pKa 4.84); hydrofluoric acid, HF, (pKa 3.20); isocitrate, $H_8(C_6O_7)$ (pKa 3.29); lactic acid, $H(C_3H_5O_3)$, (pKa 3.08); maleic acid, $H_4(C_4O_4)$ (pKa 1.83); nicotinic acid, $H_5(C_6NO_2)$ (pK 3.39); oxalic acid form 1, $H_2(C_2O_4)$, (pKa 1.23); oxalic acid form 2, $(HC_2O_4)^-$, (pKa 4.19); pentanoic acid, $H(C_5H_9O_2)$, (pKa 4.84); phosphoric acid form 1, $H_3PO_4$, (pKa 2.16); propanoic acid, $H(C_3H_5O_2)$, (pKa 4.86); pyruvic acid, $H4(C_3O_3)$ (pKa 2.39); and succinic acid $H_6(C_4O_4)$ (pKa 4.19).

3. A composition of claim 2, wherein the glycolipid is a compound of Formula II (b)

Formula II(b)

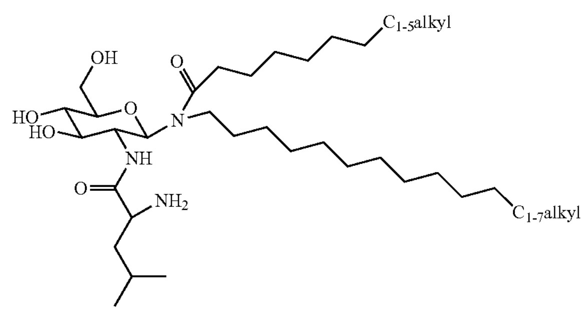

and the weak acid is selected from one or any combination of the following weak acids:

Acetic acid, acetylsalicylic acid; citric acid; formic acid; fumaric acid; hydrofluoric acid; isocitrate; maleic acid; nicotinic acid; phosphoric acid; pyruvic acid; and succinic acid.

4. A composition of claim 3, wherein the glycolipid in the salt form is N-(2-deoxy-2-L-leucylamino-β-D-glucopyranosyl)-N-octadecyldodecanamide acetate, wherein the glycolipid has a structure of Formula III:

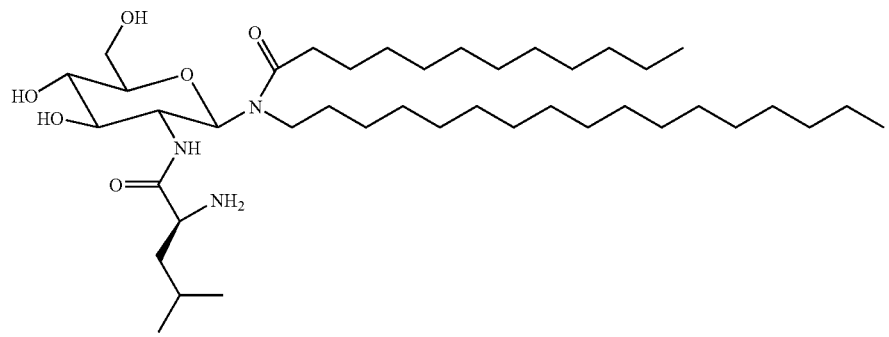

Formula III and the weak acid of part c) is acetic acid.

5. A composition of claim 2, where the weak acid is selected from the group consisting of: acetic acid; acetylsalicylic acid; citric acid form 1; citric acid form 2; citric acid form 3; formic acid; fumaric acid; hydrofluoric acid; isocitrate; maleic acid; nicotinic acid; phosphoric acid form 1; pyruvic acid, and succinic acid, or any combination thereof.

6. A composition of claim 5, where said weak acid is 1.25 times greater than the molar equivalent of the glycolipid.

7. A composition of claim 1, where said weak acid is 2.0 times greater than the molar equivalent of the glycolipid.

8. A composition of claim 1, where said weak acid is 2.5 times greater than the molar equivalent of the glycolipid.

9. A composition of claim 1, where said weak acid is 2.7 times greater than the molar equivalent of the glycolipid.

10. A composition of claim 1, where said weak acid is 3.0 times greater than the molar equivalent of the glycolipid.

11. A composition of claim 6, wherein the alcohol is ethyl alcohol.

12. A composition of claim 11, wherein said non-ionic surfactant is selected from any one of the group consisting of: Sorbitan monolaurate, Sorbitane monopalmitate, Sorbitane monostearate, Sorbitane tristearate, Sorbitane monooleate, Sorbitane trioleate, Polyoxyethylensorbitan monolaurate, Polyoxyethylensorbitan monopalmitate, Polyoxyethylensorbitan monosterate, Polyoxyethylensorbitan monooleate, and Polyoxyethylensorbitan trioleate, or a combination thereof.

13. A composition of claim 1, further comprising an aqueous buffer, wherein the buffer is suitable for vaccine use and can maintain the pH of the other ingredients within a pH range of about 6 to about 8, with the proviso that not more than 50 mM NaCl is used.

14. A composition of claim 13, where the pH of the solution is adjusted to a relatively constant pH in an aqueous solution of between about 6 and about 7, and the buffer is selected from the group consisting of a phosphate buffer having either or both monobasic and dibasic salts of sodium phosphate and a phosphate buffer having either or both monobasic and dibasic salts of potassium phosphate, at the same or different proportions, or any combination thereof.

15. A composition of claim 13, where said buffer is selected from the group consisting of:

a) 2-(N-morpholino) ethanesulfonic acid;

b) 3-(N-morpholino) propanesulfonic acid;

c) n-tris(hydroxymethyl)-2-aminoethanesulfonic acid;

d) 4-(2-hydroxyethyl)piperazine-1-ethanesulfonic acid;

e) tris(hydroxymethyl)methylglycine; and f) sodium or potassium phosphate; or any combination thereof.

16. A composition of claim 13 further comprising an antigen selected from the group consisting of modified live bovine herpes virus, modified live bovine respiratory syncytial virus, and modified live parainfluenza virus 3, or any combination thereof.

17. A composition of claim 16, wherein a) the glycolipid in the salt form is N-(2-deoxy-2-L-leucylamino-β-D-glucopyranosyl)-N-octadecyldodecanamide acetate, wherein the glycolipid has a structure of Formula III:

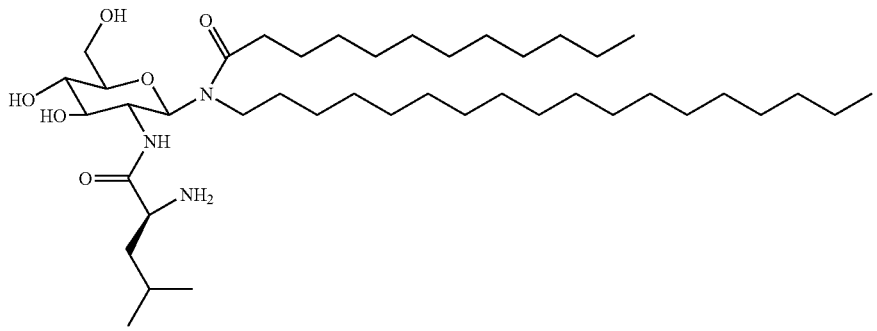

Formula III b) the alcohol is ethanol;

c) the weak acid is acetic acid;

d) the non-ionic surfactant is selected from Sorbitan monolaurate, Sorbitane monopalmitate, Sorbitane monostearate, Sorbitane tristearate, Sorbitane monooleate, Sorbitane trioleate, Polyoxyethylensorbitan monolaurate, Polyoxyethylensorbitan monopalmitate, Polyoxyethylensorbitan monosterate, Polyoxyethylensorbitan monooleate, and Polyoxyethylensorbitan trioleate, or any combination thereof;
e) the aqueous buffer can maintain the solution to a relatively constant pH of between about 6 and about 7, and the buffer is selected from the following:
   1) 2-(N-morpholino) ethanesulfonic acid,
   2) 3-(N-morpholino) propanesulfonic acid,
   3) n-tris(hydroxymethyl)-2-aminoethanesulfonic acid,
   4) 4-(2-hydroxyethyl)piperazine-1-ethanesulfonic acid, and
   5) tris(hydroxymethyl)methylglycine, or any combination thereof, and;
f) the antigen consists essentially of modified live bovine herpes virus, modified live bovine respiratory syncytial virus, and modified live parainfluenza virus 3.

18. A process for the preparation of a composition of claim 1, comprising mixing together the following:
a) the glycolipid;
b) the alcohol;
c) the weak acid; and
d) the non-ionic surfactant.

19. A process for the preparation of a composition of claim 13, comprising mixing together the following:
a) the glycolipid;
b) the alcohol;
c) the weak acid;
d) the non-ionic surfactant;
and then adding the aqueous buffer.

* * * * *

UNITED STATES PATENT AND TRADEMARK OFFICE
CERTIFICATE OF CORRECTION

PATENT NO. : 8,460,679 B2  Page 1 of 1
APPLICATION NO. : 11/698335
DATED : June 11, 2013
INVENTOR(S) : Mannan et al.

It is certified that error appears in the above-identified patent and that said Letters Patent is hereby corrected as shown below:

In the Claims

Column 23, Claim 1, Formula I structure,

" 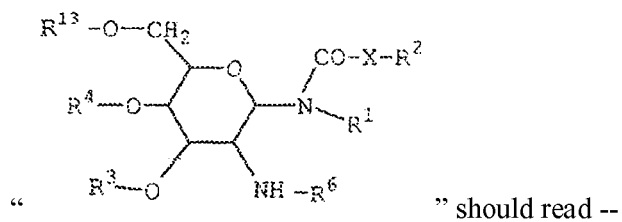 " should read -- 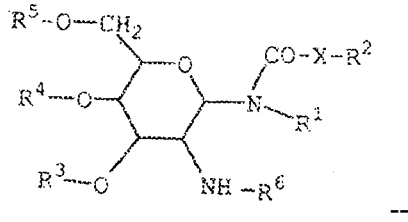 --

Column 24, line 39 (claim 2), "H4(C₃O₃)" should read -- $H_4(C_3O_3)$ --

Column 27, line 12, please insert at the end of the line and before "f)":

-- with the proviso that not more than 15 mM NaCl is used and; --

Signed and Sealed this
Seventeenth Day of June, 2014

Michelle K. Lee
*Deputy Director of the United States Patent and Trademark Office*